United States Patent
Igci et al.

(10) Patent No.: US 10,214,486 B2
(45) Date of Patent: Feb. 26, 2019

(54) PROCESS AND REACTOR SYSTEM FOR OXIDIZING CYCLOALKYLBENZENE

(71) Applicant: ExxonMobil Chemical Patents Inc., Baytown, TX (US)

(72) Inventors: Yesim Igci, Spring, TX (US); Bryan A. Patel, Jersey City, NJ (US); Min Chang, Belmont, CA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/576,919

(22) PCT Filed: Jun. 3, 2016

(86) PCT No.: PCT/US2016/035773
§ 371 (c)(1),
(2) Date: Nov. 27, 2017

(87) PCT Pub. No.: WO2017/003643
PCT Pub. Date: Jan. 5, 2017

(65) Prior Publication Data
US 2018/0148406 A1   May 31, 2018

Related U.S. Application Data

(60) Provisional application No. 62/186,981, filed on Jun. 30, 2015.

(51) Int. Cl.
| | | |
|---|---|---|
| *C07C 407/00* | (2006.01) | |
| *B01J 4/00* | (2006.01) | |
| *B01J 8/00* | (2006.01) | |
| *B01J 10/00* | (2006.01) | |
| *B01J 8/22* | (2006.01) | |

(52) U.S. Cl.
CPC ............. *C07C 407/00* (2013.01); *B01J 4/004* (2013.01); *B01J 8/22* (2013.01); *B01J 10/00* (2013.01); *C07C 2601/14* (2017.05)

(58) Field of Classification Search
CPC ...... C07C 407/00; C07C 409/14; B01J 4/004; B01J 8/22; B01J 10/00
See application file for complete search history.

(56) References Cited

U.S. PATENT DOCUMENTS

| | | |
|---|---|---|
| 6,037,513 A | 3/2000 | Chang et al. |
| 6,720,462 B2 | 4/2004 | Kuhnle et al. |
| 9,586,898 B2 | 3/2017 | Dakka et al. |
| 2004/0241059 A1 | 12/2004 | Seidlitz et al. |

FOREIGN PATENT DOCUMENTS

| | | |
|---|---|---|
| CA | 2 128 053 C | 9/2000 |
| CN | 1356161 A | 7/2002 |
| CN | 101869819 A | 12/2014 |
| WO | 2005/077526 A | 8/2005 |
| WO | 2010/074779 A | 7/2010 |
| WO | 2012/134549 A | 10/2012 |
| WO | 2012/145029 A | 10/2012 |
| WO | 2014/137623 A | 9/2014 |
| WO | 2017/003644 A | 1/2017 |

*Primary Examiner* — Sikarl A Witherspoon
(74) *Attorney, Agent, or Firm* — Kevin M. Faulkner (57) ABSTRACT

Disclosed are processes and systems for oxidizing cycloalkylbenzene such as cyclohexylbenzene to make an oxygenate such as a hydroperoxide thereof. A liquid distributor having multiple liquid ingress ports is used for supplying a cycloalkylbenzene-containing liquid into an oxidation reactor in the form of liquid streams forming part of the reaction medium. A gas distributor distributing an $O_2$-containing gas into the reaction medium in the form of gas streams is preferably located below the liquid distributor. Preferably the gas bubbles upwards in the reaction medium. The agitation and mixing provided by the liquid streams, gas streams/bubbles result in sufficient homogeneity of cycloalkylbenzene concentration, cycloalkylbenzene hydroperoxide concentration, dissolved oxygen concentration, and temperature in the liquid phase.

25 Claims, 6 Drawing Sheets

PROCESS AND REACTOR SYSTEM FOR OXIDIZING CYCLOALKYLBENZENE

CROSS REFERENCE TO PRIORITY CLAIM

This application is a National Phase Application claiming priority to PCT Application Ser. No. PCT/US2016/035773 filed Jun. 3, 2016 and U.S. Application Ser. No. 62/186,981 filed Jun. 30, 2015, the disclosures of which are fully incorporated herein by their references.

FIELD

The present invention relates to processes and reactor systems for oxidizing cycloalkylbenzene. In particular, the present invention relates to processes and reactor systems for oxidizing cyclohexylbenzene by contacting liquid cyclohexylbenzene with an $O_2$-containing gas. The present invention is useful, e.g., in making cyclohexylbenzene hydroperoxide from oxidizing cyclohexylbenzene and making phenol and cyclohexanone from cyclohexylbenzene oxidation.

BACKGROUND

The production of phenol and/or cyclohexanone from cyclohexylbenzene is an emerging technology, interesting in that it co-produces cyclohexanone, rather than acetone. Cyclohexylbenzene may be produced, for example, by direct alkylation of benzene with cyclohexene, or as disclosed in U.S. Pat. No. 6,037,513, by contacting benzene with hydrogen in the presence of a catalyst. The cyclohexylbenzene may then be oxidized to the corresponding hydroperoxide and the hydroperoxide cleaved to phenol and cyclohexanone using a catalyst. Depending upon need or demand, the phenol and cyclohexanone may each be taken as products, and/or the phenol can be hydrogenated to produce additional cyclohexanone, and/or the cyclohexanone can be dehydrogenated to produce additional phenol. Cyclohexanone is widely used to make caprolactam, which, in turn, is used for making nylon-6, a widely used polymer material. Phenol may be used to make a wide variety of chemical products, including bis-phenol A, polycarbonates, phenolic resins, and the like.

In such processes for the co-production of phenol and cyclohexanone, the oxidation of cyclohexylbenzene to cyclohexylbenzene hydroperoxide may be a gas-liquid oxidation that takes place through a free radical chain reaction catalyzed by an N-hydroxy-substituted cyclic imide, such as N-hydroxyphthalimide (NHPI), for instance as described in WO 2014/137623. In particular, a cyclohexylbenzene-containing liquid and an $O_2$-containing gas (such as pure $O_2$, air, and diluted air and $O_2$) may be supplied into an oxidation reactor, where they are allowed to contact each other, such that the cyclohexylbenzene is oxidized by $O_2$ molecules either at the gas-liquid interface and/or in the liquid phase. Inside the liquid reaction medium, along with the desired oxidation route which forms cyclohexyl-1-phenyl-1-hydroperoxide (hereinafter "1-CHB-HP), a number of side reactions may occur simultaneously producing various undesirable byproducts. It has been found that both the conversion of cyclohexylbenzene and selectivity toward 1-CHB-HP is highly dependent on the temperature of the reaction medium. Also, if temperature in a hot spot rises to an exceedingly high level, the hydroperoxide product may decompose. Due to the exothermic nature of the oxidation reactions, temperature non-uniformity inside the liquid reaction medium may occur, especially during periods of process upset where agitation produced by the $O_2$-containing gas supplied into the reactor body is reduced, leading to the formation of undesirable levels of byproducts and potentially unsafe reaction conditions.

Thus, careful design of the oxidation process and oxidation reactor is needed to reduce undesirable side reactions and the formation of byproducts.

SUMMARY

We have found that by providing a liquid distributor housed inside the oxidation reactor body configured to supply a cyclohexylbenzene-containing liquid into the reactor body, preferably at a location in the lower part of the reactor body, and more preferably above a gas distributor supplying the $O_2$-containing gas into the reactor body, the liquid reaction medium inside the reactor body above the liquid distributor is agitated at least partly by the flowing liquid supplied from the liquid distributor, even during process upsets where gas supply through the gas distributor is reduced to a less than optimized level, a high level of cyclohexylbenzene concentration uniformity, cyclohexylbenzene hydroperoxide concentration uniformity, oxygen concentration uniformity, and temperature uniformity in the liquid reaction medium above the liquid distributor can be achieved, thereby obtaining desired conversion and selectivity of the overall oxidation process.

In one aspect, the present invention provides a process for oxidizing cycloalkylbenzene in an oxidation reactor comprising a reactor body and a liquid distributor housed inside the reactor body, the process comprising: (I) supplying a cycloalkylbenzene-containing liquid through the liquid distributor into the reactor body; and (II) contacting the cycloalkylbenzene-containing liquid with an $O_2$-containing gas in the reactor body; wherein the liquid distributor is arranged such that during normal operation of the oxidation reactor: (a) the liquid reaction medium inside the reactor body above the liquid distributor is agitated at least partly by the flowing liquid supplied from the liquid distributor; and (b) the liquid reaction medium at least 10 centimeters above the liquid distributor has a concentration variation of the cycloalkylbenzene not higher than 20%.

In another aspect, the present invention provides a reactor system for oxidizing cycloalkylbenzene to produce cycloalkylbenzene hydroperoxide, comprising: (A) a reactor body configured to allow a liquid reaction medium comprising cycloalkylbenzene to contact a $O_2$-containing gas; (B) a liquid distributor housed inside the reactor body configured to supply a cycloalkylbenzene-containing liquid into the reactor body to form part of the reaction medium; (C) a gas distributor housed inside the reactor body configured to supply the $O_2$-containing gas into the reactor body; and (D) an outlet attached to the reactor body configured to draw an outgoing stream of the liquid reaction medium from inside the reactor body.

The process and reactor system of the present invention may be suitable for gas-liquid oxidation of any liquid-phase oxidizable organic compound to produce an oxygenate product thereof, such as the oxidation of cycloalkylbenzenes, to produce oxygenates thereof, and preferably, the oxidation of cyclohexylbenzene to produce hydroperoxide thereof.

DETAILED DESCRIPTION

The present disclosure provides processes and oxidation reactor systems for the oxidation of an organic compound in liquid phase by an $O_2$-containing gas featuring distributing a liquid containing the organic compound into the reactor body of the reactor system through a liquid distributor. The distribution of the liquid into the reactor body, typically in the forms of flowing streams such as jets, provides kinetic energy to the reaction medium that agitates the liquid reaction medium inside the reactor body. Preferably, the reactor processes and oxidation reactor systems also feature a gas distributor (which may be also referred as a sparger) configured to supply the $O_2$-containing gas into the reaction medium. The $O_2$ molecules at least partly diffuse into the liquid reaction medium, enabling direct contact between the organic compound molecules and the $O_2$ molecules at the liquid/gas interface and in the liquid phase. Additional kinetic energy contained in the $O_2$-containing gas distributed into the reaction medium may also provide additional agitation. It is foreseen that the during the operation of the oxidation processes and oxidation reactor systems, the supply of the $O_2$-containing gas stream may be interrupted or reduced in flow rate, such that the agitation introduced through the $O_2$-containing gas stream is minimal. According to the present disclosure, as a result of the use of the liquid distributor, sufficient agitation can be provided by the flow of the liquid supplied into the reactor body alone.

The processes and reactor systems provided herein are particularly suited for gas-liquid oxidation of organic compounds having relatively slow reaction kinetics, and/or gas-liquid oxidation reactions in which per-pass conversion is desirably low (e.g., less than 50% conversion of the organic compounds to be oxidized). A particular example of such a reaction, as noted above and also as described in greater detail below, is the oxidation of cyclohexylbenzene to form cyclohexylbenzene hydroperoxide, especially 1-CHB-HP. The processes and reactor systems of the present invention will be described below in the context of cyclohexylbenzene oxidation. However, one having ordinary skill in the art would readily appreciate that the processes and reactors for cyclohexylbenzene oxidation described below can be readily adapted for use in the oxidation of other cycloalkylbenzene and other organic compounds.

Furthermore, such an oxidation reaction (and systems and apparatus for carrying out such a reaction) may, according to some embodiments, form an integral part of a larger overall process for the co-production of cyclohexanone and phenol from cyclohexylbenzene produced by the alkylation or hydroalkylation of benzene. Major steps of the overall process are described below as well.

Supply of Cyclohexylbenzene

The cyclohexylbenzene supplied to the oxidation can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

(Reaction-1)

Alternatively, cyclohexylbenzene can be produced by direct alkylation of benzene with cyclohexene in the presence of a solid-acid catalyst such as molecular sieves in the MCM-22 family according to the following Reaction-2:

(Reaction-2)

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 types described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials and/or binders. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, $SnO$, $SnO_2$, and mixtures, combinations and complexes thereof.

The effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants.

Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Transalkylation with additional benzene is desirably effected in a transalkylation reactor, which is separate from the hydroalkylation reactor, over a suitable transalkylation catalyst, such as a molecular sieve of the MCM-22 type, zeolite beta, MCM-68 (see U.S. Pat. No. 6,049,018), zeolite Y, zeolite USY, and mordenite. The transalkylation reaction is desirably conducted under at least partially liquid phase conditions, which suitably include a temperature in the range from 100° C. to 300° C., a pressure in the range from 800 kPa to 3500 kPa, a weight hourly space velocity from 1 hr$^{-1}$ to 10 hr$^{-1}$ on total feed, and a benzene/dicyclohexylbenzene weight ratio in a range from 1:1 to 5:1.

Dealkylation is also desirably effected in a reactor separate from the hydroalkylation reactor, such as a reactive distillation unit, at a temperature of about 150° C. to about 500° C. and a pressure in a range from 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is desirably introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene, and a heavies fraction which can be subjected to a transalkylation/dealkylation reaction again or discarded.

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

Oxidation of Cyclohexylbenzene

In the oxidation of cyclohexylbenzene, cyclohexylbenzene is converted to 1-phenyl-1-cyclohexyl hydroperoxide, otherwise referred to herein as 1-CHB-HP, the desired hydroperoxide, according to the following Reaction-3:

(Reaction-3)

Other undesirable hydroperoxides may simultaneously form in the oxidation process of cyclohexylbenzene. To increase the selectivity toward 1-CHB-HP, a catalyst, such as the oxidation catalysts described in Paragraphs [0050]-[0054] of WO 2014/137623. A particularly suitable type of catalyst is N-substituted cyclic imides, such as N-hydroxyphthalimide (NHPI).

The reaction is preferably carried out as a gas-liquid reaction, with the cyclohexylbenzene in the liquid phase being contacted by an oxygen-containing gas. This may be accomplished, e.g., by passing the oxygen-containing gas through the liquid-phase reaction medium comprising the cyclohexylbenzene (for instance, as in a bubble column reactor). The $O_2$ molecules in the gas diffuses into the liquid phase. Reaction-3 may occur at the interface of the gas phase and the liquid phase and inside the liquid phase between the $O_2$ molecules and the cyclohexylbenzene molecules.

However, cyclohexylbenzene hydroperoxides, including the desired 1-CHB-HP, and other undesired hydroperoxides, may further react, producing undesired byproducts such as phenyhlcyclohexanols, hydroperoxy hexaphenones, and others, especially at a high concentration thereof in the reaction medium. The higher the reaction temperature, the more likely the hydroperoxides are to undergo side reactions. Thus, the temperature of the reaction medium in the reactor body is desired to be controlled at not higher than Tmax ° C., where Tmax can be 150, 145, 140, 135, 130, 125, 120, 115, 110, 105, 100, 98, 96, 95, 94, 92, or even 90. The oxidation reactions in the reaction medium are highly exothermic. Static zones in the reaction medium, due to insufficient mixing with surrounding medium, can experience local temperature significantly higher than the bulk medium as a result of the heat released and become hot spots. Such hot spots can be reduced and/or eliminated by a liquid flow regime in the reactor body ensuring sufficient agitation and mixing of the liquid, even in the absence of additional agitation caused by streams of gas supplied by the gas distributor, achieved by the present invention.

It is preferable to operate the reaction at a relatively low conversion per pass, such as a conversion of about 5 to about 30 mol % per pass, for instance about 5 to any one of about 7, 8, 9, 10, 11, 12, 13, 14, 15, 16, 17, 18, 19, or 20 mol % per pass. In some embodiments, multiple series reactions may be used. For instance, two, three, four, five or more series reactors may be used, each operating at a per-pass conversion within one of the aforementioned ranges, thereby increasing the overall conversion. Overall conversion may be about 10 to about 50 mol %, such as an overall conversion ranging from a low of any one of about 10, 15, 16, 17, 18, 19, 20, 21, 22, 23, 24, and 25 mol % to a high of any one of about 25, 26, 27, 28, 29, 30, 35, 40, 45, and 50 mol %, provided the high is greater than the low end of the range. In particular embodiments, per-pass conversion may be about 7-10 mol % (such as about 8-9 mol %) in each of one, two, or three series reactors (thereby providing an overall conversion of about 21-30 mol % (such as about 24-27 mol %) when two, three or four reactors in series are used).

Figure 1:
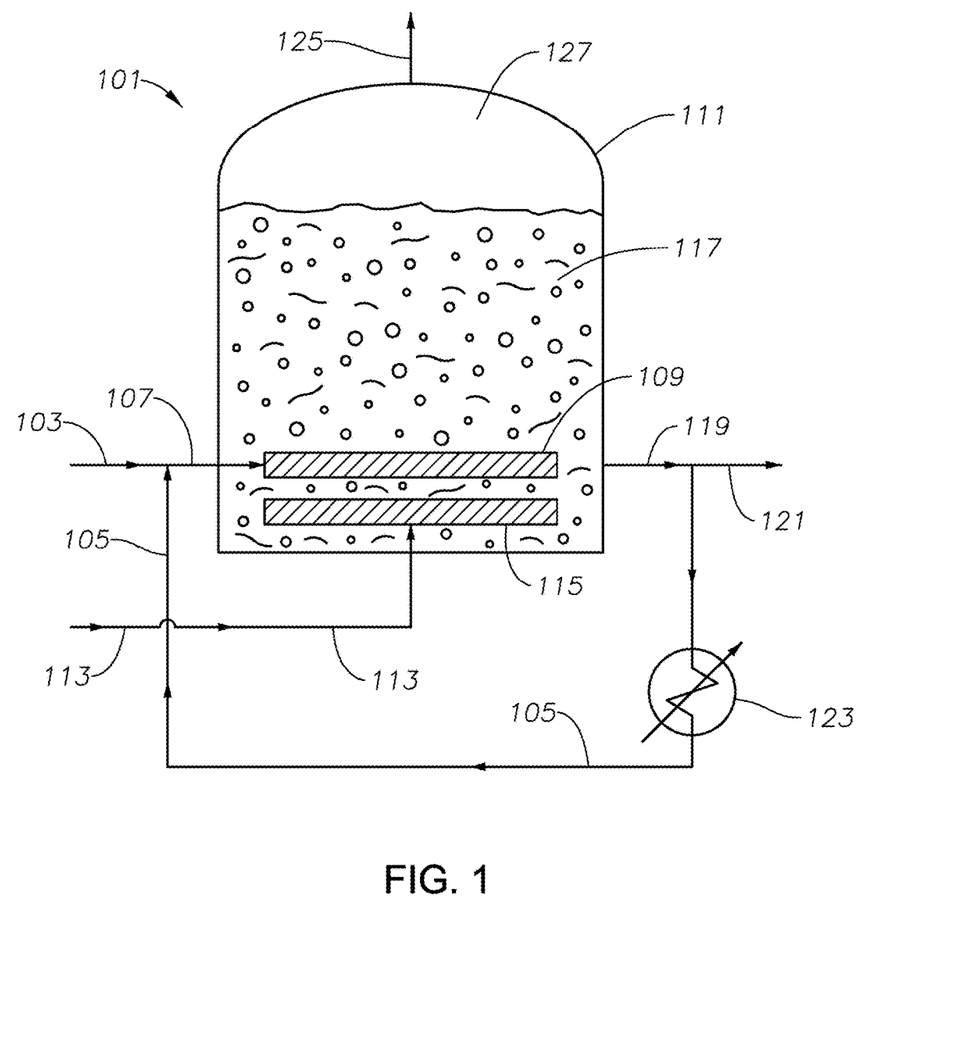
FIG. 1 is a simplified diagram illustrating an exemplary cyclohexylbenzene oxidation process and system of the present invention.

FIG. 1 schematically shows an exemplary oxidation reactor system 101 operating to oxidize liquid cyclohexylbenzene by an $O_2$-containing gas. In this figure, a fresh cyclohexylbenzene stream 103 is combined with a recycle cyclohexylbenzene-stream 105 to form a combined cyclohexylbenzene-containing liquid stream 107 comprising cyclohexylbenzene, oxidation catalyst (such as NHPI), 1-CHB-HP, and certain byproducts, and then supplied into the reactor body 111 through a liquid distributor 109 to form a part of the liquid reaction medium 117 inside the reactor body. The liquid distributor 109 has multiple holes, orifices, nozzles, and/or ports (collectively referred to as "liquid ingress ports" herein), through which the cyclohexylbenzene-containing liquid enters into the reaction medium as liquid jet streams. A stream 113 of $O_2$-containing gas, such as air, modified air, diluted $O_2$, and the like, is supplied into the reactor body through a gas distributor 115, which is located below the liquid distributor 109. The gas distributor also has multiple orifices, holes, nozzles, and/or ports (collectively referred to as "gas ingress ports" herein) through which the $O_2$-containing gas enters the reaction medium as gas jet streams. The gas jet streams form multiple bubbles traveling upwards through the reaction medium in the reactor body. The kinetic energy carried by the liquid jet streams and the gas jet streams and rising bubbles agitate the reaction medium 117, such that a desired flow pattern, a high degree of mixing of the reaction medium, and desired concentration profiles in the reaction medium, are achieved. The $O_2$ molecules diffuse from the gas streams and bubbles into the liquid phase of reaction medium. In the liquid phase and at the gas-liquid interface, cyclohexylbenzene molecules react with the $O_2$ molecules to form, among others, the desired 1-CHB-HP product. An outgoing stream of reaction medium 119 is withdrawn from an outlet on the side wall of the reactor body, a portion of which is sent to the next step/reactor as stream 121, and a portion of which is cooled by a heat exchanger 123 to remove a portion of the heat generated by the oxidation reactions, and then, as a recycle stream 105, combined with fresh cyclohexylbenzene stream 103 to form a combined cyclohexylbenzene-containing liquid stream 107, and then supplied to the oxidation reactor body through the liquid distributor 109 as described above. An oxidation catalyst as described above (such as NHPI) is preferably supplied to the liquid phase reaction medium, either with the feed (such as stream 103 and/or stream 105) or separately. Residual gas, typically with a reduced $O_2$ partial pressure than the $O_2$-gas stream 113, due to consumption of $O_2$ in the reaction medium, exits the reaction medium, collects at the top space 127 of the reactor body, and subsequently exits the reactor body as a gas stream 125. The reactor may be operated at any hydrodynamic flow regimes. However, homogeneous (bubbly) flow regime provides good gas and liquid contacting and is preferred for commercial performance.

FIG. 1 shows a single oxidation reactor vessel in the system. In practice, multiple reactor vessels with substantially the same or different designs may be connected in series or in parallel, or both, and used in an overall oxidation system, to achieve an overall degree of oxidation of cyclohexylbenzene with desired level of conversion of cyclohexylbenzene and selectivity toward 1-CHB-HP. The multiple reactor vessels may be equipped with substantially the same type of liquid distributors, gas distributors, and operate under the same or different reaction conditions, including temperature, catalyst type, catalyst concentration, residence time, and the like.

Liquid Distributor

Theoretically, the cycloalkyl-containing liquid (such as a cyclohexylbenzene-containing liquid) can be supplied into the oxidation reactor body via any port located anywhere on the reactor body wall. However, preferably, a liquid distributor located inside the housing of the oxidation reactor body is used, through which one or more streams of the feed liquid is ejected into the reactor body forming part of the liquid reaction medium. Preferably, the liquid distributor is submerged in the liquid reaction medium during normal operation of the oxidation process.

As shown in FIG. 1, the oxidation reactor system may comprise components operable to withdraw and pump a portion of its contents through a suitable cooling device such as a heat exchanger and return the cooled portion to the reactor, thereby managing the heat release of the reactions taking place in the reaction medium. In FIG. 1, the recycle reaction mixture stream 105 is combined with fresh cyclohexylbenzene stream 103 before being delivered to a single liquid distributor 109. It is possible, however, that the fresh cyclohexylbenzene stream and the recycle reaction medium stream are supplied into the reactor body via separate liquid distributors, which may be of the same or different types, disposed inside the reactor body.

The amount of liquid, including the fresh cyclohexylbenzene feed and recycle reaction medium feed, supplied to the reactor relative to the reactor volume depends on operating parameters, such as temperature, pressure, target conversion, and selectivity. The amount of recycle reaction medium relative to the amount of fresh cyclohexylbenzene liquid feed depends on the designed heat exchanger duty. The recycle ratio, defined as the weight ratio of the recycle reaction medium stream (105) to the fresh cyclohexylbenzene stream (103), can range from r1 to r2, where r1 and r2 can be, independently, 0.1, 0.2, 0.4, 0.5, 0.6, 0.8, 1.0, 1.5, 2.0, 2.5, 3.0, 3.5, 4.0, 4.5, 5.0, 7.5, 10, 15, 20, 25, 30, 35, 40, 45, 50, 55, 60, 65, 70, 75, 80, as long as r1<r2.

In order to achieve the desired conversion and selectivity in the reactor while maintaining operational safety, good oxygen distribution and liquid mixing across the reactor cross-section is highly desired. The liquid distributor design can strongly influence the gas and liquid circulation and mixing of both gas and liquid species in the oxidation reactor. Moreover, the liquid distributor design desirably provides effective mixing in the reactor, either in the presence or in the absence of gas supply to ensure rapid and effective cool down of the reactor.

The liquid distributor used for the oxidation reaction may be any type that allows for introduction of liquid feed and/or recirculation streams to the reactor, and may further efficaciously provide contacting of oxygen and cyclohexylbenzene to effect the oxidation reaction. For example, the liquid distributor may be a perforated plate distributor, a porous plate distributor, a membrane distributor, a perforated pipe distributor, an arm-network distributor, or a ring type distributor network with multiple jets.

Depending on the choice of liquid distributor design, the flow patterns and the mass transfer between the gas and liquid phased can vary significantly. A liquid distributor network with multiple jets is one preferred embodiment to ensure the desired hydrodynamics in the reactor vessel and ensure sufficient mixing either in the presence or in the absence of gas supply, and irrespective of the flow rate of the gas.

Figure 2:
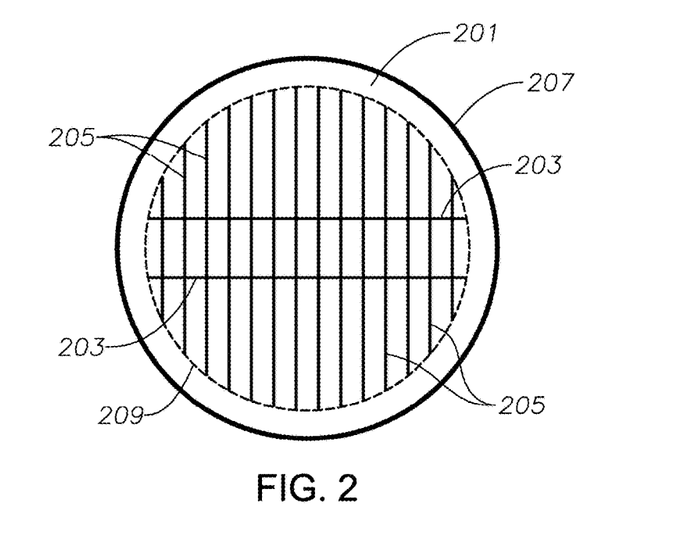
FIG. 2 is a schematic illustration of an exemplary arm-network liquid distributor useful in the present invention.

In an exemplary arm-network liquid distributor according the present invention that is illustrated in FIG. 2 (showing a plan view of an arm-and-header type liquid distributor), the liquid distributor 201 typically comprises a network of conduits comprising header conduits 203 and arm conduits 205. The arm conduits 203 (and optionally the header conduits 205) has multiple liquid ingress ports thereon. The conduits may be in direct or indirect fluid communication with one another, such that the liquid is distributed throughout the entire network of conduits. The center lines of the conduits may be substantially within a horizontal plane that is substantially perpendicular to the gravity acceleration vector.

Figure 3A:
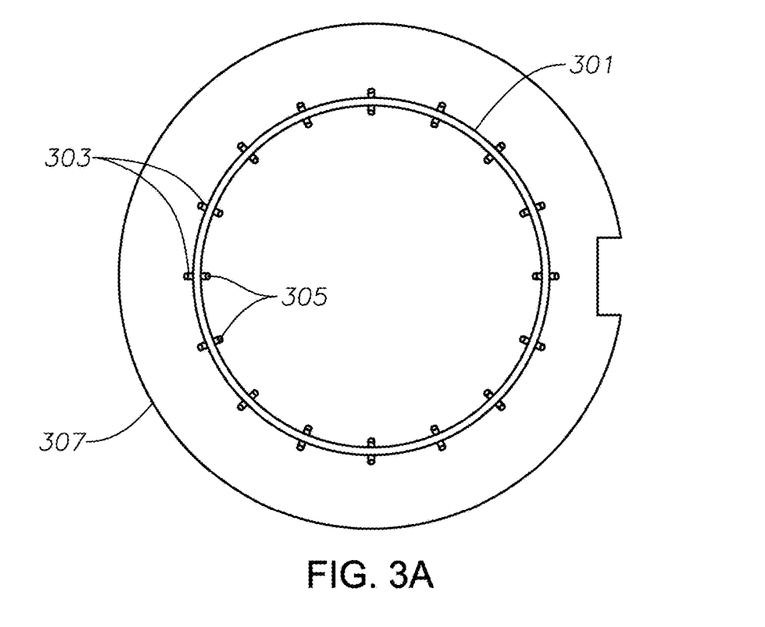
FIGS. 3A, 3B, and 3C are schematic illustrations of different views of a ring-type liquid distributor useful in the present invention.
Figure 3B:
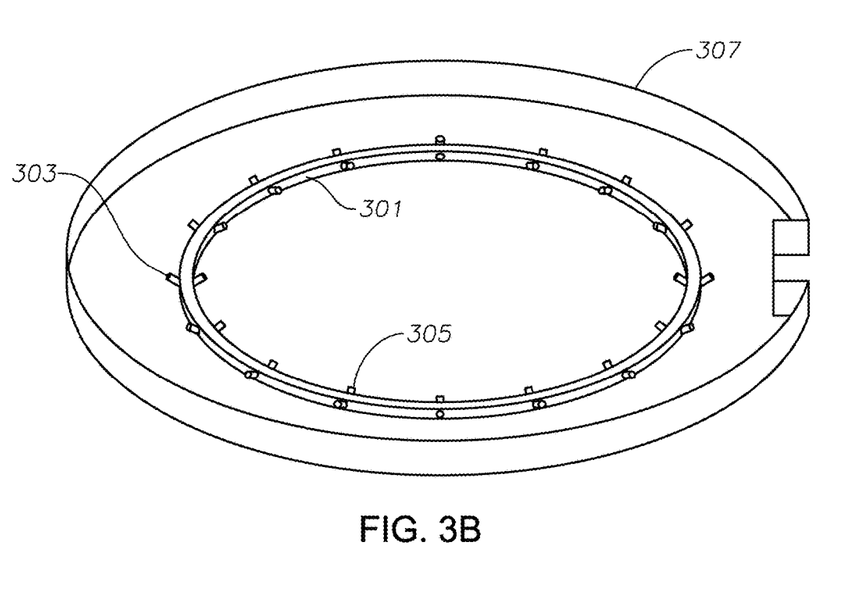
Figure 3C:
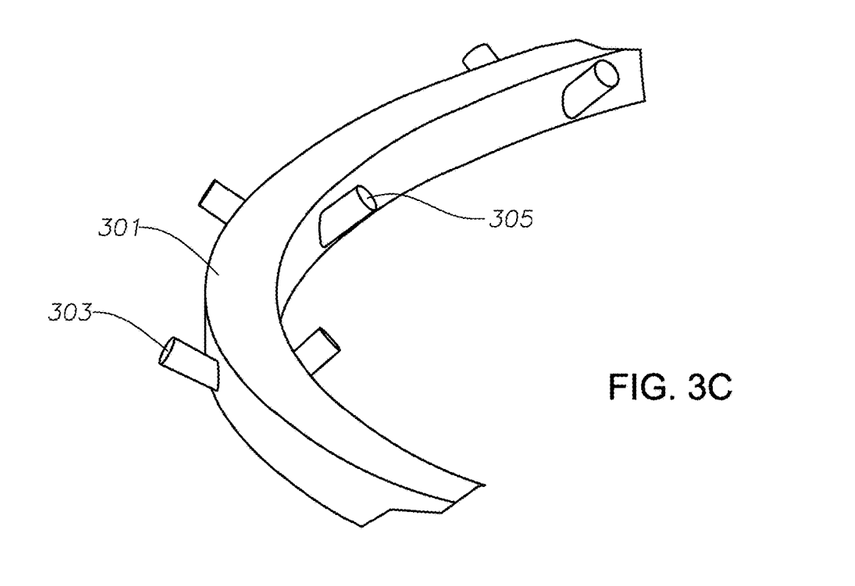

FIGS. 3A, 3B, and 3C schematically show different views of a ring-type liquid distributor useful in the present invention. This liquid distributor has a ring-shaped header conduit 301, which can conveniently reside inside a substantially cylindrically shaped reactor body 307. A plurality of liquid distribution nozzles 305, pointing outward, are affixed to the inner rim of the header conduit 301, and a plurality of nozzles 303, pointing inward, are affixed to the outer rim of the header conduit 301. During operation, liquid jet streams ejected from nozzles 303 are projected away from the center of the reactor body and toward the inner wall of the reactor body; and liquid jet streams ejected from nozzles 305 are projected toward the center of the reactor body and away from the inner wall.

Figure 4A:
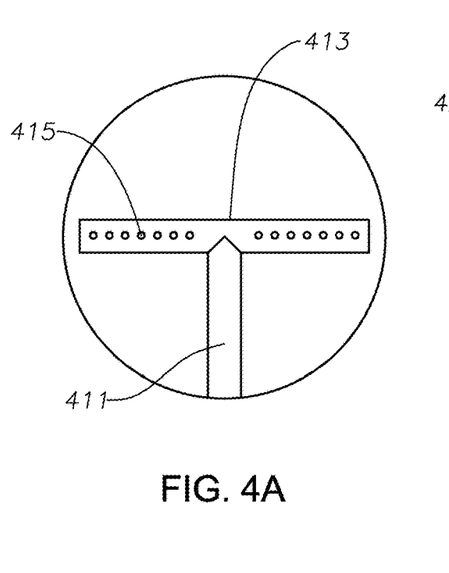
FIGS. 4A, 4B, and 4C are schematic illustrations of different additional designs of liquid distributors useful in the present invention.
Figure 4B:
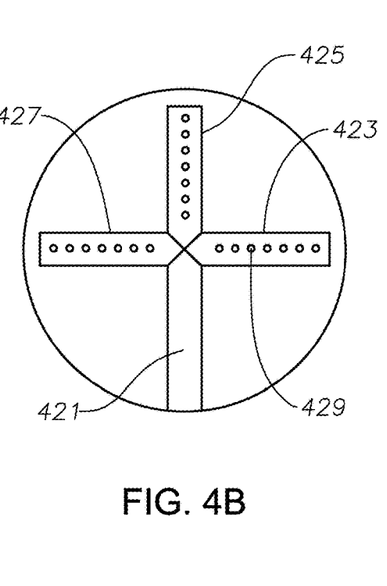
Figure 4C:
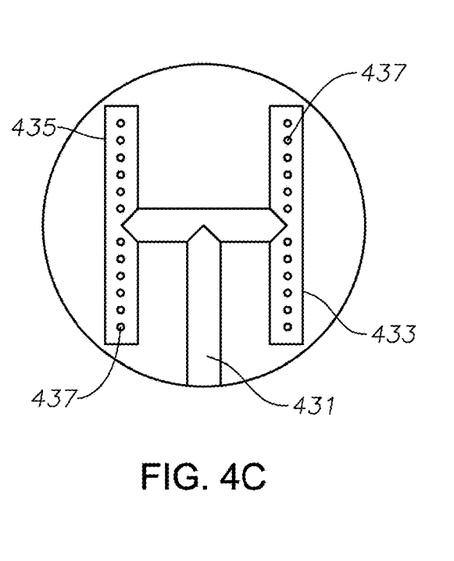

FIGS. 4A, 4B, and 4C are schematic illustrations of various designs of perforated pipe liquid distributor with holes thereon. In these designs, 411, 421, and 431 are header conduits, 413, 423, 427, 433, and 435 are pipes with holes 415, 429, and 437 as liquid ingress ports. These different designs can be advantageously used in reactors with different sizes, geometries, and different operating conditions such as temperature, pressure, catalyst type, catalyst concentration, and the like.

In general, liquid distributor headers, arms, concentric rings may be of any size (length, width, thickness, and diameter), any shape or any number. They may be oriented in any direction within the reactor.

For a ring-type distributor network, the main header may be located anywhere in the reactor. Additionally, it may be oriented in any direction within the reactor. For the ring type distributor, the distributor network may comprise of one or more concentric ring headers with one or more jets emanating from it. In the design shown in FIGS. 3A and 3B, there are one ring and 32 jets. It is preferred to have multiple jets, rather than a single jet since a single jet tends to form a strong recirculation zone trapping gas and creating oxygen depleted zones. For a ring-type distributor design, the liquid distributor header may of any shape and size (thickness and height) between 0.1 inch and the reactor diameter. For example, it can be 10 inches in thickness (diameter) and height.

The conduits of the liquid distributor having the liquid ingress ports disposed within the reactor body may have inner diameter within a range from a low of any one of about 0.01, 0.02, 0.03, 0.04, 0.05, 0.06, 0.07, 0.08, 0.09, and 0.10 meter, to a high of any one of about 0.06, 0.07, 0.08, 0.09, 0.10, 0.15, 0.20, 0.25, 0.30, 0.35, 0.40, 0.45, 0.50, 0.60, 0.70, 0.80, 0.90, and 1.0 meter. In some embodiments, the conduits have approximately equal (+/−5% from average) diameters. Alternatively, the conduits may have varying diameter. Typically, header conduits tend to have larger diameters than arm conduits in arm-network liquid distributors.

Each liquid ingress port may have a diameter of about 2 mm to about 250 mm. Size of the liquid ingress ports can be determined according to the total flow rate and pressure of the cyclohexylbenzene-containing liquid supplied into the reactor body, the total number of the liquid ingress ports, and the like. Diameter of the liquid ingress port (defined as the diameter of the smallest circle that the inner cross-section of the liquid ingress port can fit into) may range from Dlip1 millimeters to Dlip2 millimeters, where Dlip1 and Dlip2 can be, independently, 2, 4, 5, 6, 8, 10, 20, 30, 40, 50, 60, 70, 80, 90, 100, 120, 140, 150, 160, 180, 200, 220, 240, 250, as long as Dlip1<Dlip2.

Liquid streams are ejected into the reactor body through the liquid ingress ports, forming part of the reaction medium inside the oxidation reactor. Each liquid ingress port can be oriented independently such that the liquid stream can be ejected upwards, downwards, toward the center of the reactor body, or away from the center of the reactor body. The liquid ingress ports may be stationery enabling a fixed angle of the liquid stream ejected therefrom, or adjustable (movable) enabling changing angle of the liquid stream ejected therefrom. The liquid ingress ports may be oriented such that the multiple liquid streams ejected from them may combine to establish a desirable flow pattern inside the reaction medium and achieve a desirable distribution profile of cyclohexylbenzene, oxygen, 1-CHB-HP, and temperature therein.

The average liquid velocity per nozzle may be between 0.1 and 100 m/s. Nozzle velocity (or flow rate) affects for mixing, particularly in the absence of gas supply. Therefore, it is preferred that the average liquid velocity per nozzle is between 0.2 and 5 m/s. Depending on the liquid flow rate fed to the reactor, the desired liquid velocity per nozzle also sets a design criteria for number of nozzles for the single ring-type distributor.

The liquid distributor may be designed in a way such that nozzle velocities may be different. It is preferred that they are the same. The jets may be all oriented inward or outward or some inward and some outward. It is preferred that some jets are oriented towards the reactor walls while others are oriented away from the walls to mix the core of the reactor vessel. For a ring-type distributor design, the liquid distributor header may be located anywhere in the reactor. It is preferred that it is located at a place where the total areas serviced by the inward and outward nozzles are the same. The openings (e.g. nozzles) may be of any size (internal diameter) between 0.01 inch and the reactor diameter. The distance between the nozzles may be between 0.01 inch and the reactor diameter. Distance between jets (nozzles) may be the same, meaning the distance between all nozzles oriented in or outward are equal to 360 degrees divided by the number of nozzles oriented inward or outward, or different. It is preferred that the distance is somewhat uniform. The inward and outward jets may be staggered or aligned along the pipe. Jets (nozzles) may be located anywhere with the liquid distributor or oriented in any direction (upward, downward, 45 degrees, etc.), though it is preferred to orient the nozzles at an orientation between that parallel to the reactor bottom (90°) and that pointing directly towards the reactor top (0°).

The liquid distributor may contain any number of drainage holes through which liquid material can flow out of the distributor conduits due to gravity in case emptying the reactor body and/or the distributor conduits is needed.

Preferably, a liquid distributor is disposed within a lower portion of the oxidation reactor housing defined by the reactor body. As used herein, a "lower portion" of the oxidation reactor housing refers to the bottom ¼ of the reactor volume. That is, for a reactor with a height of H meters, the "lower portion" of the reactor encompasses the volume within the reactor from the bottom of the reactor to a horizontal plane perpendicular to the gravity acceleration vector, which is located 0.25*H meters above the bottom of the reactor. The liquid distributor may be disposed at a height that is from about 0.01 H to about 0.25 H, such as 0.015 H to about 0.20 H, preferably about 0.015 H to about 0.15 H, such as about 0.015 H to about 0.10 H, where H is the height of the reactor body in which the liquid distributor is disposed. The liquid distributor has one or more holes, orifices, nozzles, and/or ports (collectively referred to as "liquid ingress ports" herein) through which the cyclohexylbenzene-containing liquid is delivered into the reactor body forming part of the reaction medium.

As used herein, a "cross-section of the reactor body" is defined as an area enclosed by a closed curve obtained by intersecting the inner wall of the reactor body by a horizontal plane perpendicular to the gravity acceleration vector. As used herein, the diameter of a cross-section of the reactor body at a given height is defined as the diameter of the smallest circle capable of enclosing the cross-section of the reactor body at the given height. Preferably, vertically projected images of the liquid ingress ports on the horizontal cross-section of the reactor body are distributed within a circle (209 in FIG. 2) with the smallest possible area A(min), where A(min) is in a range from p1 % to p2 % of the total area of the horizontal cross-section at the height of the lowest liquid ingress port, where p1 and p2 can be, independently, 50, 55, 60, 65, 70, 75, 80, 85, 90, 95, 96, 98, 99, or even 100, as long as p1<p2. Preferably, the distribution of the images of the ingress ports on the horizontal cross-section at the height of the lowest liquid ingress port is substantially even. Preferably, the distances from the vertically projected images of the outmost liquid ingress ports on the horizontal cross-section at the height of the lowest liquid ingress port to the center of the cross-section are substantially uniform. Thus, assuming the average of the distances from the vertically projected images of the outmost liquid ingress ports to the center of the horizontal cross-section is r(av), the actual shortest distances from the projected images of the outmost liquid ingress ports to the center of the horizontal cross-section is in the range from 0.80*r(av) to 1.20*r(av), preferably from 0.90*r(av) to 1.10*r(av), and even more preferably from 0.95*r(av) to 1.05*r(av). Preferably, the shortest distances from the vertically projected images of the outmost liquid ingress ports on the horizontal cross-section at the height of the lowest liquid ingress port to the periphery of the cross-section are substantially uniform.

Thus, assuming the average of the shortest distances from the vertically projected images of the outmost liquid ingress ports to the periphery of the horizontal cross-section is s(av), the actual shortest distances from the projected images of the outmost liquid ingress ports to the periphery of the horizontal cross-section is in the range from 0.80*s(av) to 1.20*s(av), preferably from 0.90*s(av) to 1.10*s(av), and even more preferably from 0.95*s(av) to 1.05*s(av).

The reactor body may have a substantially circular, elliptical, or polygonal horizontal cross-section at the height of the lowest liquid ingress port. The diameter of the smallest circle in which the horizontal cross-section at the height of the lowest liquid ingress port can fit is defined as the diameter of the reactor body. The diameter of the reactor body may range from D1 meters to D2 meters, where D1 and D2 can be, independently, 0.1, 0.2, 0.4, 0.5, 0.6, 0.8, 1.0, 2.0, 4.0, 5.0, 6.0, 8.0, 10, 15, 20, 25, 30, 35, 40, 45, 50, 55, 60, 65, 70, 75, 80, as long as D1<D2. The reactor body may have a height from the bottom to the top in the range from H1 meters to H2 meters, where H1 and H2 can be, independently, 1.0, 2.0, 4.0, 5.0, 6.0, 8.0, 10, 15, 20, 25, 30, 35, 40, 45, 50, 55, 60, 65, 70, 75, or 80, as long as H1<H2.

During operation, the reaction medium may have a liquid depth from the top of the reaction medium to the bottom of the reactor body in a range from Dp1 meters to Dp2 meters, where Dp1 and Dp2 can be, independently, 0.1, 0.2, 0.4, 0.5, 0.6, 0.8, 1.0, 2.0, 4.0, 5.0, 6.0, 8.0, 10, 15, 20, 25, 30, 35, 40, 45, 50, 55, 60, as long as Dp1<Dp2. In general, from the top of the liquid reaction medium inside the reactor body to the top of the reactor body, a space is reserved for collecting residual gas exiting the reaction medium. The residual gas has an $O_2$ partial pressure lower than in the gas supplied to the reaction medium through the gas distributor described in greater detail below.

As a result of the use of a liquid distributor housed inside the reactor body, effective mixing of the reaction medium inside the reactor body and desired flow profile of the reaction medium can be achieved, without the need of a mechanical stirrer providing additional agitation to the reaction medium, either in the presence of a gas stream supplied to the reaction medium, or in the absence thereof. It is contemplated, however, that additional mechanical stirrer, in the form of one or more propellers and the like, may be installed in the reactor body where necessary to achieve the desired level of agitation, mixing, and homogenization of the reaction medium.

As a result of the function of the liquid distributor and optionally the gas distributor, substantially homogeneous concentrations of cyclohexylbenzene, 1-CHB-HP, and/or $O_2$ in the liquid phase of the reaction medium above the liquid distributor can be achieved. Thus, the variation of one or more of (i) cyclohexylbenzene concentration and (ii) 1-CHB-HP concentration in the liquid phase of the reaction medium at least 10 centimeters above the liquid distributor can be at most 20%, 18%, 16%, 15%, 14%, 12%, 10%, 8%, 6%, 5%, 4%, or even 2%. Furthermore, the variation of dissolved $O_2$ in the liquid phase of the reaction medium at least 10 centimeters above the liquid distributor can be at most 30%, 28%, 26%, 25%, 24%, 22%, 20%, 18%, 16%, 15%, 14%, 12%, 10%, 8%, 6%, 5%, 4%, or even 2%. As used herein, variation of concentration (Vcon) of a particular component is defined as the percentage of the difference between (a) the time-averaged concentration (in a period of e.g., 10 hours, 8 hours, 5 hours, 4 hours, 3 hours, 2 hours, or 1 hour) at a given location (Cloc) at least 10 centimeters above the liquid distributor and (b) the average (Cav) of the time-averaged concentrations of all liquid medium at least 10 centimeters above the liquid distributor relative to the average concentration (Cav):

$$Vcon = \frac{|Cloc - Cav|}{Cav} \times 100\%.$$

A low variation of one of these concentrations indicate good mixing of the reaction medium, and substantially even conversion of cyclohexylbenzene in the liquid phase in the reaction medium at least 10 centimeters above the liquid distributor. A distance "above the liquid distributor" herein means distance from the highest liquid ingress port located on the liquid distributor, irrespective of the other structure of the liquid distributor and location thereof. As a result of the good mixing of the reaction medium, a low variation of temperature (Vt) of at most 10° C., 9° C., 8° C., 7° C., 6° C., 5° C., 4° C., 3° C., 2° C., or even 1° C., among the liquid medium at least 10 centimeters above the liquid distributor is also achieved. As used herein, variation of temperature (Vt) is defined as the difference between (a) the time-averaged temperature (in a period of e.g., 10 hours, 8 hours, 5 hours, 4 hours, 3 hours, 2 hours, or 1 hour) at a given location (Tloc) at least 10 centimeters above the liquid distributor and (b) the average (Tav) of the time-averaged temperatures of all liquid medium at least 10 centimeters above the liquid distributor:

$$Vt=|Tloc-Tav|.$$

Such low temperature variation indicates the minimization of hot spot within the liquid reaction medium, which is especially desirable for suppressing undesirable side reactions, including but not limited to those involving decomposition of 1-CHB-HP, and the formation of other, undesirable cyclohexylbenzene hydroperoxides.

When the oxidation reactor of the present invention operates during normal mode, liquid feeds, including fresh cyclohexylbenzene feed and recycle reaction medium stream, are supplied to the reactor body as multiple jets forming part of the liquid reaction medium, and preferably the $O_2$-gas stream is bubbled through the gas distributor into the reaction medium. The kinetic energy entrained by the liquid streams and the gas bubbles cause agitation, mixing, and homogenization of the reaction medium inside the reactor body. During the operation of the overall process, there may be occasions where the gas supply is shut off, reduced in flow rate, accidentally or intentionally. At the beginning of the cut-off of gas supply, due to dissolved $O_2$ in the liquid phase, oxidation reactions continue which release heat. The reduced agitation as a result of loss of gas supply to the reaction medium could cause hot spot formation if the remaining agitation in the liquid medium was insufficient. The present invention, by utilizing liquid distributor inside the reactor body, ensures sufficient and proper agitation in the liquid reaction medium in such events and achieves a high homogeneity in concentrations and temperature distribution.

Where the reactor is equipped with both a liquid distributor and a gas distributor, the liquid distributor can be located, in part or in whole, below or above the gas distributor. Preferably, however, the liquid distributor is at least partly located above the gas distributor because this arrangement results in better agitation and mixing of the liquid reaction medium in the reactor body, improved contact between the gas phase and the liquid phase, and higher homogeneity of the reaction medium during normal operation where gas is supplied to the reaction medium. By "at least partly located above the gas distributor," it is meant that at least a portion of the liquid ingress ports is/are located above at least a portion of the ports on the gas distributor through which the gas enters the reaction medium. It is desired, however, that both the gas distributor and the liquid distributor are located in the lower portion of the reactor body. To that end, if a liquid distributor is located completely above the gas distributor, it is desired that the distance between the highest gas ingress port on the gas distributor and the lowest liquid ingress port on the liquid distributor is in a range from d1 meter(s) to d2 meter(s), where d1 and d2 can be, independently, 0.01, 0.02, 0.04, 0.05, 0.06, 0.08, 0.10, 0.15, 0.20, 0.25, 0.30, 0.35, 0.40, 0.45, 0.50, 0.55, 0.60, 0.65, 0.70, 0.80, 0.85, 0.90, 0.95, 1.0, 1.2, 1.4, 1.5, 1.6, 1.8, 2.0, as long as d1<d2.

$O_2$ concentration in liquid phase of the reaction medium of several different cyclohexylbenzene oxidation reactors obtained through computational fluid dynamics (CFD) simulations are illustrated in FIGS. 5A, 5B, 6A, and 6B. In these figures, color uniformity is an indicator of $O_2$ concentration uniformity in the liquid phase of the reaction medium. Concentration of $O_2$ in the liquid phase correlates with the wavelength of the visible light with the color shown at a location of the reaction medium. Thus, red represents a high $O_2$ concentration in the liquid phase, yellow a lower $O_2$ concentration than red, green even a lower $O_2$ concentration than yellow, with the deepest blue the lowest concentration, i.e., essentially zero.

Figure 5A:
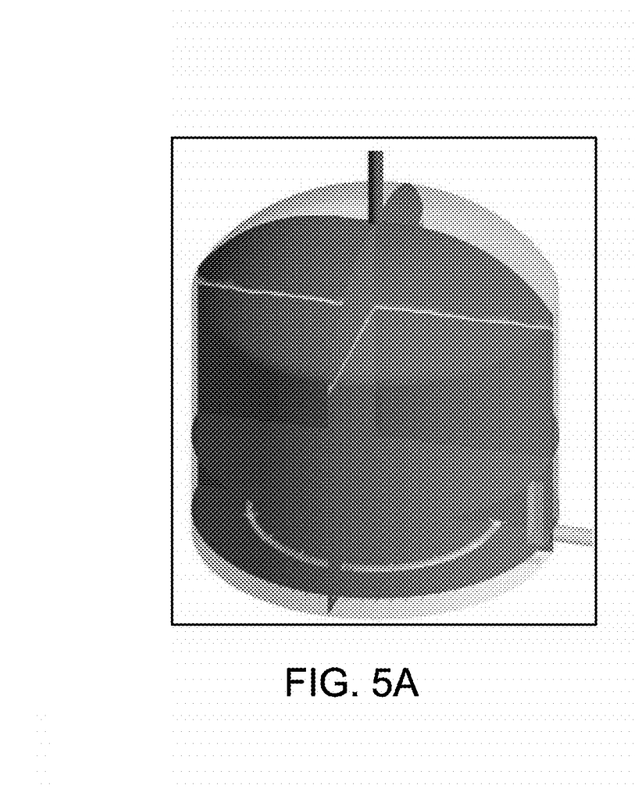
FIGS. 5A and 5B are diagrams showing oxygen concentration profiles of an exemplary cyclohexylbenzene oxidation reactor operating according to the present invention.
Figure 5B:
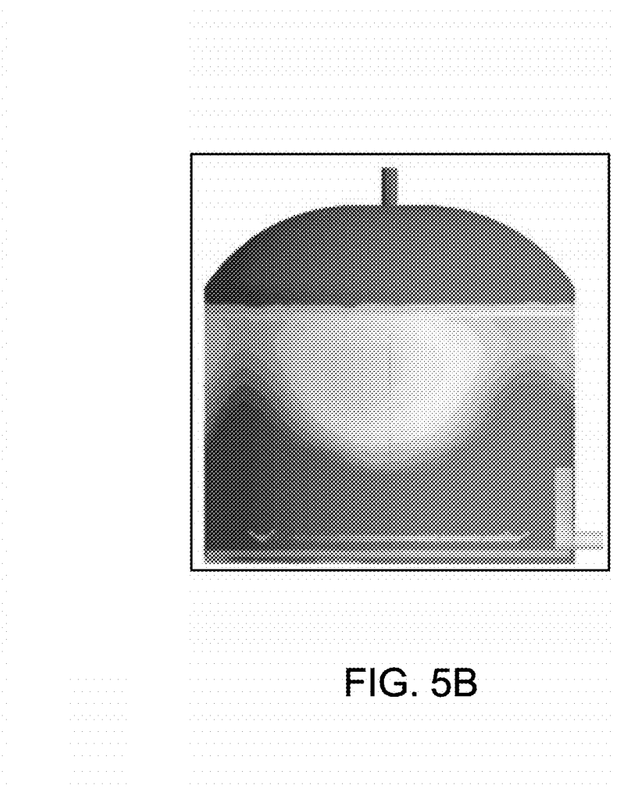

FIGS. 5A and 5B show the results of a CFD simulation of a characteristic geometry for an oxidation reactor equipped with a liquid distributor illustrated in FIGS. 3A, 3B, and 3C located in proximity to the bottom of the reactor body and a gas distributor located below the liquid distributor, indicating time averaged oxygen concentration profile within the reactor. FIGS. 5A and 5B are results at two different scale levels. It is apparent that there are no oxygen starved zones ($X_{O2}/X_{O2}$*<1) in the liquid rich regions (with less than 50% gas holdup), where the bulk of the reaction takes place. FIGS. 5A and 5B demonstrate that the framework of the liquid distributor described herein provides sufficient uniformity of oxygen in liquid phase for reactor performance Additionally, mixing time studies (with liquid tracers in CFD) with this design showed that liquid phase provides good liquid mixing in the reactor in the absence of gas.

Figure 6A:
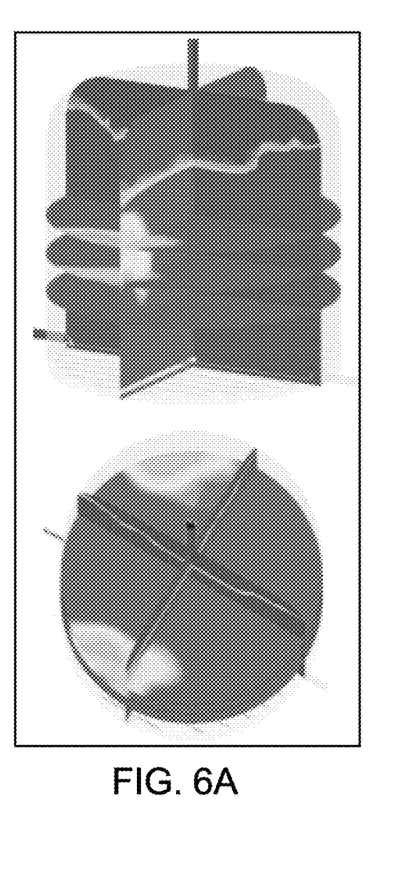
FIGS. 6A and 6B are diagrams showing oxygen concentration profiles of comparative cyclohexylbenzene oxidation reactors without using a liquid distributor.
Figure 6B:
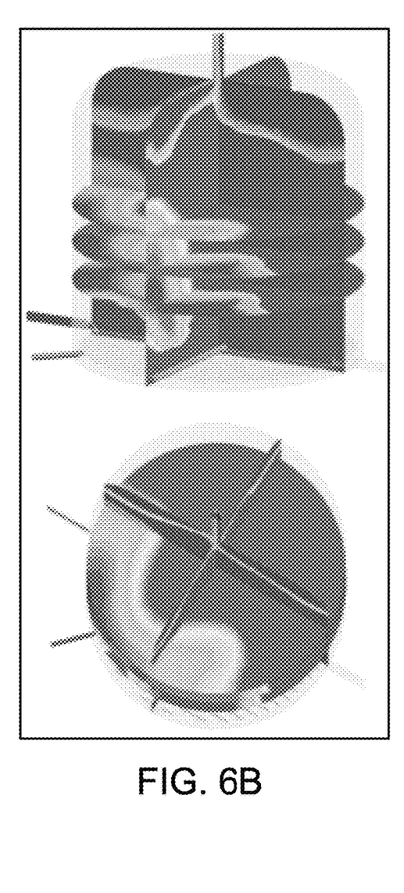

FIGS. 6A and 6B are schematic drawings of a cyclohexylbenzene oxidation reactor without a liquid distributor located in proximity of the bottom of the reactor body, but with a side wall inlet for fresh feed and recycle streams. In this particular design, the two liquid streams are introduced to the oxidation reactor separately. The CFD simulations of this geometry and an only fresh feed case (no recycle, FIG. 6A) demonstrated that side entrance jets create oxygen depleted zones and this effect is amplified by increase in recycled liquid rate (FIG. 6B). In the case with recycle (FIG. 6B), the total liquid feed entering the reactor is several times more than the no-recycle case.

Gas distribution and gas distributor in the reactor system are described in detail below.

Gas Distribution and Gas Distributor

Preferably, the gas is distributed into the liquid-phase reaction medium such that in any given continuous area of 10.0 centimeters by 10.0 centimeters inside (i) a first horizontal cross-section of the liquid-phase reaction medium, and/or (ii) a second horizontal cross-section of the liquid-phase reaction medium, the average quantity of oxygen passing through the given continuous area per second (QO1) is in a range from 60% to 140% of QO2, where QO2 is the average quantity of oxygen passing through the whole given horizontal cross-section, expressed in terms of quantity of oxygen per 100 square centimeters per second. Even more preferably, QO1 is in a range from 80% to 120% of QO2.

Furthermore, the gas in some embodiments is distributed such that the oxygen concentration [$O_2$] at either or both of the horizontal cross sections is greater than a threshold oxygen concentration [$O_2$*] throughout the reaction medium (that is, such that [$O_2$]/[$O_2$.]>1). The threshold oxygen concentration is the localized concentration of oxygen in the liquid phase above which the reaction becomes independent of oxygen concentration (i.e., such that oxygen concentration is no longer a bottleneck to the rate and/or extent of reaction). The threshold oxygen concentration depends upon temperature and oxidation catalyst (e.g., NHPI) concentration. The threshold oxidation concentration will also depend upon the particular liquid-phase oxidation reaction taking place. Threshold oxygen concentration may be readily determined for any given temperature and oxidation catalyst concentration by studying reaction rates for varying oxygen concentrations and determining the concentration above which no change in reaction rate occurs.

Each horizontal cross section is, respectively, a cross-sectional area in a plane that is substantially parallel to the bottom of the reactor. As used herein, "substantially parallel" in reference to another plane, line, conduit, component, or the like, means +/−10° (with 0° being exactly parallel). When used in the special case of "horizontal" planes, components, or cross sections, "substantially parallel" in particular means +/−10° with respect to the normal of the expected gravity vector where the reactor is located. The first horizontal cross section is X centimeters above the top of the gas distributor, while the second horizontal cross section is Y centimeters above the top of the gas distributor (where Y>X).

In various embodiments, X may be less than or equal to any one of 5, 10, 15, 20, 25, 50, 75, and 100 centimeters (i.e., such that the first horizontal cross section is less than or equal to 5, 10, 15, 20, 25, 50, 75, and 100 centimeters above the top of the gas distributor). In various embodiments, Y may be greater than or equal to any one of 100, 200, 300, 400, 500, and 600 centimeters, provided that Y is greater than X.

The relatively uniform distribution of oxygen through a given cross-section of the liquid-phase reaction medium described by these embodiments enables highly efficient utilization of the oxygen within the oxygen-containing gas passing through the liquid-phase reaction medium, which helps minimize the amount of oxygen bypass, thereby resulting in adequately low concentration of oxygen in the vapor-phase overhead. This is so despite the desirably low per-pass conversion in the reaction, and the slow reaction kinetics.

Distributing the oxygen-containing gas in some embodiments maintains the overhead oxygen concentration at safe levels well below the flammability limit of 10.5 vol %. Preferably, the oxygen concentration in the overhead vapor phase is maintained at or below 8.0 vol %, more preferably at or below 5.0 vol %.

In some embodiments, the gas distributor through which the oxygen-containing gas is delivered into the liquid-phase reaction medium has one or more particular features. In certain embodiments, the aforementioned relatively uniform distribution of oxygen gas in the reaction medium is achieved through the use of a gas distributor according to such embodiments.

A gas distributor according to some embodiments is disposed within a lower portion of the oxidation reactor. As used herein, a "lower portion" of the oxidation reactor refers to the bottom ¼ of the reactor. That is, for a reactor of dispersed liquid height H meters, the "lower portion" of the reactor encompasses the volume within the reactor from the bottom of the reactor to a plane parallel to the reactor bottom, which is located 0.25*H meters above the bottom of the reactor. As used herein, reference to the gas distributor being "disposed in" the reactor at a given height (or range of heights) indicates the distance between (1) the reactor bottom and (2) the bottom-most portion of the gas distributor. For instance, where some components of the gas distributor are disposed lower in the reactor than other components, the lowest components are used for measurement of height at which the gas distributor is disposed.

In particular embodiments, where dispersed liquid height in the reactor is about 0.1 ft to about 50 ft (about 0.03 to about 15.24 m), the gas distributor may be disposed within the reactor such that it is elevated about 0.01 to about 3.81 m from the bottom of the reactor.

In some embodiments, dispersed liquid height may be 0.1 ft to any one of about 10, 12, 15, 17, 20, 22, and 25 ft (0.03 m to any one of about 3.05, 3.66, 4.57, 5.18, 6.10, 6.71, and 7.62 m). The cost of gas compression may be a driving factor to maintaining relatively low dispersed liquid height in such embodiments. However, in yet other embodiments, dispersed liquid height may range from about 15 to 35 ft (about 4.57 to 10.67 m), such as about 15 to 25 ft (about 4.57 to about 7.62 m), since each foot of liquid height allows more liquid to fit in a single reactor (thereby allowing a reactor of equal diameter to hold more liquid phase reaction medium, and therefore provide a greater amount of product per pass). In addition, maintaining adequate height according to such embodiments may help maintain circulation of reactants within the liquid phase reaction medium.

A gas distributor may comprise a network of conduits through which the oxygen-containing gas may flow. The network of conduits can comprise header conduits and arm conduits connected to the header conduits. The conduits may be in direct or indirect fluid communication with one another, such that the oxygen-containing gas is distributed throughout the entire network of conduits. The network of conduits may be disposed within a plane that is substantially parallel to the bottom of the reactor. The smallest possible area within this plane that may be defined so as to encompass the network of conduits is considered the "gas distributor horizontal cross-sectional area". A plurality of orifices is disposed along the conduits and within the distributor horizontal cross-sectional area. Preferably, the distributor horizontal cross-sectional area is from 70 to 95% of the cross-sectional area of the lower portion of the oxidation reactor in which the gas distributor is disposed (that is, the cross-sectional area of the reactor in a plane, or top-down, view). This may be referred to as 70 to 95% "distributor coverage." Put in mathematical terms, where the reactor has inner cross-sectional area A square meters in the plane in which the gas distributor is disposed, the gas distributor cross-sectional area is preferably 0.7 A m² to 0.95 A m². More preferably, the distributor coverage is about 75% to about 95% of the cross-sectional area of the lower portion of the oxidation reactor in which the gas distributor is disposed, such as about 75% to any one of 80%, 85%, 90%, and 95%; or about 80% to any one of about 85% and 90%.

Where the reactor body is cylindrical about an axis, the gas distributor horizontal cross-sectional area is preferably centered about the same axis, such that the space between the reactor inner wall and the outer edge of the gas distributor horizontal cross-sectional area is roughly equal along the entire interior surface of the reactor wall. "Roughly equal" allows for deviations, at any given position, of up to 5% of the average distance between reactor side wall and outer edge of the gas distributor horizontal cross-sectional area.

The conduits of the gas distributor may have inner diameter within a range from a low of any one of about 0.01, 0.02, 0.03, 0.04, 0.05, 0.06, 0.07, 0.08, 0.09, and 0.10 m, to a high of any one of about 0.06, 0.07, 0.08, 0.09, 0.10, 0.15, 0.20, 0.25, 0.30, 0.35, 0.40, 0.45, 0.50, 0.60, 0.70, 0.80, 0.90, and 1.0 m. In some embodiments, the conduits have approximately equal (+/−5% from average) diameters. The conduits may have varying diameter. There may be conduits of at least 2, 3, 4, 5, or more different diameters in the network of conduits forming the gas distributor. For instance, arm-and-header type gas distributors may comprise header conduits, having diameter $D_1$, and arm conduits, having different diameter $D_2$, representing an embodiment with conduits of 2 different diameters. The header diameter $D_1$ of such embodiments may be at least 2, 3, 4, or 5 times greater than the arm diameter.

With respect to the orifices disposed along the conduits, in some embodiments, there are on average 0.1 to 10 of the orifices per square foot (about 1.076 to 107.6 orifices per $m^2$) within the gas distributor horizontal cross-sectional area. Preferably, there are on average 0.5 to 5 orifices per square foot (5.38 to 53.8 orifices per $m^2$); more preferably on average about 1 to 3 orifices per square foot (about 10.76 to about 32.29 orifices per $m^2$), such as about 2 orifices per square foot (21.53 per $m^2$). The qualifier "on average" indicates that the orifices in such embodiments are not necessarily distributed evenly within the distributor horizontal cross-sectional area. However, in some embodiments, the orifices are evenly distributed within the gas distributor horizontal cross-sectional area (meaning that the spacing between any two orifices is approximately equal to the spacing between any other two orifices). In such embodiments, the spacing between each orifice is about 0.05 to about 0.25 m. For instance, the spacing between each orifice may range from a low of any one of about 0.05, 0.06, 0.07, 0.08, 0.09, 0.1, 0.11, 0.12, 0.13, and 0.14 m to a high of any one of about 0.10, 0.11, 0.12, 0.13, 0.14, 0.15, 0.16, 0.17, 0.18, 0.19, 0.20, and 0.25 m, provided the high end of the range is greater than the low end. For example, the spacing between any two orifices may be about 0.10 m to about 0.20 m, such as about 0.12 to about 0.18 m, or 0.14 m to about 0.19 m, and so on.

Each orifice may have a diameter of about 2 mm to about 10 mm. Orifice diameter may be determined with respect to a desired size for bubbles of the oxygen-containing gas to be released into the liquid-phase reaction medium. Orifice diameter may range from a low of any one of about 1, 2, 3, 4, and 5 mm, to a high of any one of about 3, 4, 5, 6, 7, 8, 9, 10, 11, 12, 13, 14, and 15 mm, provided the high end of the range is greater than the low end. For non-circular orifices, diameter may be approximated as the average distance between pairs of edge points along the orifice, the pairs of edge points joined by a line that intersects the center of the orifice.

The orifices may be any opening disposed along the conduits through which the oxygen-containing gas can flow into the liquid-phase reaction medium. Preferably, the orifices are nozzles. The nozzles of such embodiments may optionally extend outward from the conduit, extending away from a conduit (shown as a head-on cross-section of an arm conduit). The nozzles of such embodiments may further have a particular orientation. In general, the nozzles may be oriented at any angle between −90° and +90° (where 90° is in the plane of the gas distributor horizontal cross-sectional area). Thus, in general, each nozzle may be oriented such that the oxygen-containing gas is ejected from the nozzle in (i) a direction within the plane of the distributor horizontal cross sectional area, (ii) a direction perpendicular to the distributor horizontal cross sectional area and toward a bottom of the oxidation reactor, or (iii) a direction at any angle therebetween. The nozzles may be oriented at least partially downward (that is, toward a bottom surface of the reactor). For instance, the nozzle may be oriented so as to eject gas downward at an angle between −60° and +60°, where 0° is a normal vector directed at the reactor bottom surface (and may also be taken as a direction perpendicular to the plane of the gas distributor horizontal cross-sectional area). Preferably, the nozzle is oriented so as to eject gas at an angle between −50° and +50° ; more preferably, about 40° to about 50° (or about −50° to about −40°). The nozzles 305 may be oriented at about 45° (or −45°) relative to the 0° vector directed into the reactor bottom. Preferably, the oxygen-containing gas, after being passed through the nozzles (or other orifices), contacts a bottom surface of the oxidation reactor at least in part, and thereafter rises upward through the liquid phase reaction medium as a plurality of bubbles.

The gas distributor may be operated within a desired range of pressure drops across the network of conduits.

Any of various arrangements of the gas distributor's network of conduits may be used to provide the necessary features (e.g., nozzles per $m^2$, coverage of the gas distributor cross-sectional area, and the like). One preferred arrangement is an arm distributor network, comprising a plurality of arm conduits coupled to one or more header conduits. In particular, the arm distributor network may comprise two header conduits, each in fluid communication with a plurality of arm conduits extending outwardly away from the headers across the gas distributor cross-sectional area. In some embodiments, the arm conduits are disposed substantially perpendicularly with respect to the header conduits within the plane of the gas distributor cross-sectional area. As used in this context, "substantially perpendicularly" means at an angle from 80° to 100° with respect to another conduit, plane, line, component, or the like (with 90° being exactly perpendicular to, i.e., at a right angle to). Alternatively, the arm conduits may run in any non-parallel direction transverse to the header conduits (e.g., at an angle from about 5° to about 175°, such as 45° to 135°, to the header conduit, with 0° measured along the direction in which the header conduit runs within the plane of the gas distributor horizontal cross-sectional area). The header conduits may run parallel to each other. Further, the arm conduits may each run parallel to each other. However, in embodiments wherein the header conduits do not run parallel to each other, any two or more header conduits may intersect at a junction such that they are in fluid communication with one another. Likewise, where arm conduits do not run parallel to each other, any two or more arm conduits may intersect at one or more junctions such that they are in fluid communication with one another.

Preferably, however, the arm conduits run parallel to one another, and the header conduits likewise run parallel to one another.

Further, in a network of arm distributors, the inner diameter of the header conduits may be greater than the inner diameter of the arm conduits. Where the header conduit inner diameter is greater than the arm conduit inner diameter, preferably the arm conduits are joined with the header conduit(s) in a manner such that the arm conduits are each centered on the header conduit(s) at junctions, such that the header conduit(s) extend farther down in the reactor. In such instances, the elevation of the gas distributor is taken as the distance from the reactor bottom to the bottom of the header conduit(s).

In some embodiments, the gas distributor comprises 1, 2, 3, 4, or 5 header conduits. Further, the gas distributor may comprise a number of arm conduits ranging from a low of any one of 10, 11, 12, 13, 14, 15, 16, 17, 18, 19, and 20 arm conduits, to a high of any one of 15, 16, 17, 18, 19, 20, 25, 30, 35, 40, 45, and 50 arm conduits, provided the high end of the range is greater than the low end of the range. For instance, the gas distributor of some embodiments may comprise 2 header conduits, each in fluid communication with a plurality of arm conduits, said plurality of arm conduits comprising from 10 to 45, such as 15 to 25, such as 23, arm conduits, said arm conduits intersecting, and in fluid communication with, both header conduits.

Any other arrangement of the network of conduits may provide the necessary features (e.g., coverage; orifice size, spacing, and amounts; conduit diameters; gas distributor elevation in the reactor; etc.). Other suitable arrangements include, but are not necessarily limited to, concentric ring spargers, porous plate spargers, membrane spargers, perforated plate distributors, perforated pipes, and the like. In general, any gas distributor arrangement suitable for use in a bubble column may be utilized to provide the necessary features.

Cleavage of Cyclohexylbenzene-Hydroperoxide

In the cleavage reaction, at least a portion of the 1-CHB-HP decomposes in the presence of an acid catalyst in high selectivity to cyclohexanone and phenol according to the following desired Reaction-4:

(Reaction-4)

The cleavage product mixture may comprise the acid catalyst, phenol, cyclohexanone, cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene. Acid catalysts preferably include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, sulfur trioxide, and solid acid catalysts such as zeolites. Sulfuric acid and solid acids are preferred acid catalysts.

The cleavage reaction can take place in a cleavage reactor in direct or indirect fluid communication with the oxidation reactor or the oxidation reactor system. The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting the cleavage reactor may comprise, based on the total weight of the cleavage product mixture: (i) phenol at a concentration from CPh11 wt % to CPh12 wt %, where CPh11 and CPh12 can be, independently, 20, 25, 30, 35, 40, 45, 50, 55, 60, 65, 70, 75, or 80, as long as Ch11<CPh12; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; and (iii) cyclohexylbenzene at a concentration from Cchb9 wt % to Cchb10 wt %, where Cchb9 and Cchb10 can be, independently, 5, 8, 9, 10, 12, 14, 15, 18, 20, 22, 24, 25, 26, 28, 30, 35, 40, 45, 50, 55, 60, 65, 70, as long as Cchb9<Cchb10.

Separation and Purification

The cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first fractionation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated form phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., WIPO publications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent fractionation column, the lower fraction can then be separated to obtain an upper fraction comprising a phenol product and a lower fraction comprising the extractive solvent.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

The invention claimed is:

1. A process for oxidizing cycloalkylbenzene in an oxidation reactor comprising a reactor body and a liquid distributor comprising liquid ingress ports, the liquid distributor housed inside the reactor body, the process comprising:
   (I) supplying a cycloalkylbenzene-containing liquid through the liquid distributor into the reactor body; and
   (II) contacting the cycloalkylbenzene-containing liquid with an $O_2$-containing gas in the reactor body;
   wherein the liquid distributor is arranged such that during normal operation of the oxidation reactor: (a) the liquid reaction medium inside the reactor body above the liquid distributor is agitated at least partly by the flowing liquid supplied from the liquid distributor; and (b) the liquid reaction medium above the liquid distributor has a concentration variation of the cycloalkylbenzene not higher than 20%.

2. The process of claim 1, wherein the cycloalkylbenzene is cyclohexylbenzene.

3. The process of claim 1, wherein the liquid distributor is located at a distance from the bottom of the reactor body in a range from 5 centimeters to 500 centimeters.

4. The process of claim 1, wherein the $O_2$-containing gas is supplied into the reactor body through a gas distributor.

5. The process of claim 1, wherein the gas distributor is located below the liquid distributor.

6. The process of claim 4, comprising a step of continuing to flow the cycloalkylbenzene-containing liquid through the liquid distributor into the reactor body where gas supply through the gas distributor into the reactor body is reduced to a level at most 50% of the level during normal operation.

7. The process of claim 1, wherein the liquid phase of the reaction medium inside the reactor body at least 10 centimeters above the liquid distributor has an $O_2$ concentration variation during normal operation of the oxidation reactor not higher than 30%.

8. The process of claim 1, wherein the liquid phase of the reaction medium inside the reactor body at least 10 centimeters above the liquid distributor has a cycloalkylbenzene hydroperoxide concentration variation not higher than 20%.

9. The process of claim 1, wherein the temperature in the liquid reaction medium inside the reactor body at least 10 centimeters above the liquid distributor has a variation not higher than 10° C.

10. The process of claim 1, wherein the liquid distributor has at least one liquid ingress port ejecting a liquid jet upwards at least partly toward the top of the reactor body.

11. The process of claim 1, wherein the liquid distributor has at least one liquid ingress port ejecting a liquid jet away from the center of the reactor body.

12. The process of claim 1, wherein the liquid distributor has at least one port ejecting a liquid jet toward the center of the reactor body.

13. The process of claim 4, wherein the gas distributor comprises at least one gas ingress port ejecting a gas stream downwards toward the bottom of the reactor body.

14. The process of claim 1, further comprising drawing an outgoing stream of the liquid reaction medium from the reactor body, and cooling and recycling a portion of the outgoing stream into the reactor body.

15. The process of claim 1, wherein the cycloalkylbenzene-containing liquid is a mixture of fresh cycloalkylbenzene and the portion of the outgoing stream recycled to the reactor body.

16. A reactor system for oxidizing cycloalkylbenzene to produce cycloalkylbenzene hydroperoxide, comprising:
   (A) a reactor body configured to allow a liquid reaction medium comprising cycloalkylbenzene to contact a $O_2$-containing gas;
   (B) a liquid distributor housed inside the reactor body configured to supply a cycloalkylbenzene-containing liquid into the reactor body to form part of the reaction medium, the liquid distributor comprising liquid ingress ports;
   (C) a gas distributor housed inside the reactor body configured to supply the $O_2$-containing gas into the reactor body; and
   (D) an outlet attached to the reactor body configured to draw an outgoing stream of the liquid reaction medium from inside the reactor body.

17. The reactor system of claim 16, wherein the liquid distributor is located at a distance from the bottom of the reactor body in a range from 5 centimeters to 500 centimeters.

18. The reactor system of claim 16, wherein the gas distributor is located at a distance from the bottom of the reactor body in a range from 0 centimeters to 450 centimeters.

19. The reactor system of claim 16, wherein the gas distributor is located below the liquid distributor.

20. The reactor system of claim 16, further comprising:
   (E) a fresh feed supply conduit configured to supply a fresh cycloalkylbenzene stream to the liquid distributor.

21. The reactor system of claim 16, further comprising:
   (F) a recycle conduit configured to supply at least a portion of the outgoing stream to the liquid distributor.

22. The reactor system of claim 16, wherein the fresh supply conduit and the recycle conduit converge to form a unitary conduit connected to the liquid distributor.

23. The reactor system of claim 16, wherein the liquid distributor is configured to produce multiple liquid jets of the cycloalkylbenzene-containing liquid through multiple liquid ingress ports projecting in different directions.

24. The reactor system of claim 16, wherein at least one of the liquid jets projects away from the center of the reactor body, and at least one of the liquid jets projects toward the center of the reactor body.

25. The reactor system of claim 16, wherein the cycloalkylbenzene is cyclohexylbenzene.

* * * * *